(12) United States Patent
Porter (10) Patent No.: US 7,645,292 B2
(45) Date of Patent: Jan. 12, 2010

(54) VASO-OCCLUSIVE DEVICES WITH IN-SITU STIFFENING ELEMENTS

(75) Inventor: Stephen C. Porter, Oakland, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 533 days.

(21) Appl. No.: 10/695,151

(22) Filed: Oct. 27, 2003

(65) Prior Publication Data
US 2005/0090861 A1    Apr. 28, 2005

(51) Int. Cl.
*A61M 29/00* (2006.01)
(52) U.S. Cl. .................. 606/200; 606/191
(58) Field of Classification Search ........... 606/108, 606/190–200, 151, 213–215; 128/887, 830–833; 424/422, 423, 484, 486
See application file for complete search history.

(56) References Cited

U.S. PATENT DOCUMENTS

| | | | |
|---|---|---|---|
| 3,174,851 A | | 3/1965 | Buchler et al. |
| 3,351,463 A | | 11/1967 | Rozner et al. |
| 3,753,700 A | | 8/1973 | Harrison et al. |
| 4,994,069 A | * | 2/1991 | Ritchart et al. ............. 606/191 |
| 5,234,437 A | | 8/1993 | Sepetka |
| 5,250,071 A | | 10/1993 | Palermo |
| 5,261,916 A | | 11/1993 | Engelson |
| 5,290,552 A | | 3/1994 | Sierra et al. |
| 5,304,195 A | | 4/1994 | Twyford, Jr. et al. |
| 5,312,415 A | | 5/1994 | Palermo |
| 5,350,397 A | | 9/1994 | Palermo et al. |
| 5,423,829 A | | 6/1995 | Pham |
| 5,456,667 A | | 10/1995 | Ham et al. |

(Continued)

FOREIGN PATENT DOCUMENTS

EP    1 290 988    3/2003

(Continued)

OTHER PUBLICATIONS

PCT International Search Report for PCT/US2004/033423, Applicant: Scimed Life Systems, Inc., Forms PCT/ISA/210 and 220, dated Feb. 24, 2005 (8 pages).

(Continued)

*Primary Examiner*—Anhtuan T Nguyen
*Assistant Examiner*—Elizabeth Houston
(74) *Attorney, Agent, or Firm*—Vista IP Law Group LLP (57) ABSTRACT

Vaso-occlusive devices for occluding a body cavity include an internal element located within a lumen of the device. The internal element may include an active element configured to stiffen the coil in-situ made from a material that can expand to a desired size, thereby inducing a radial stress to the coil to stiffen the occlusive device. Alternatively, the active element is secured to two points on the occlusive device, and is made from a material that contracts, thereby inducing a compression to stiffen the device. The internal element may additionally include an agent carrier that comprises a bioactive material capable of eliciting a biological reaction after the device is placed in-situ. For example, the bioactive material can be a part of a composition of the agent carrier, absorbed by the agent carrier, or coated as a layer on the agent carrier.

9 Claims, 6 Drawing Sheets

U.S. PATENT DOCUMENTS

| | | | |
|---|---|---|---|
| 5,582,619 | A | 12/1996 | Ken |
| 5,658,308 | A | 8/1997 | Snyder |
| 5,669,931 | A * | 9/1997 | Kupiecki et al. ............ 606/191 |
| 5,690,666 | A | 11/1997 | Berenstein et al. |
| 5,695,469 | A | 12/1997 | Segal |
| 5,749,894 | A * | 5/1998 | Engelson .................... 606/213 |
| 5,826,587 | A | 10/1998 | Berenstein et al. |
| 5,833,705 | A | 11/1998 | Ken et al. |
| 5,853,418 | A | 12/1998 | Ken et al. |
| 5,984,929 | A | 11/1999 | Bashiri et al. |
| 6,004,338 | A | 12/1999 | Ken et al. |
| 6,013,084 | A | 1/2000 | Ken et al. |
| 6,165,178 | A | 12/2000 | Bashiri et al. |
| 6,168,788 | B1 | 1/2001 | Wortham |
| 6,193,728 | B1 | 2/2001 | Ken et al. |
| 6,231,588 | B1 * | 5/2001 | Zadno-Azizi ............... 606/200 |
| 6,273,108 | B1 * | 8/2001 | Bergman et al. ......... 134/102.1 |
| 6,287,318 | B1 | 9/2001 | Villar et al. |
| 6,322,576 | B1 | 11/2001 | Wallace et al. |
| 6,375,669 | B1 * | 4/2002 | Rosenbluth et al. ......... 606/200 |
| 6,616,617 | B1 * | 9/2003 | Ferrera et al. ............... 600/585 |
| 6,629,947 | B1 * | 10/2003 | Sahatjian et al. .............. 604/13 |
| 6,790,218 | B2 * | 9/2004 | Jayaraman .................. 606/191 |
| 6,953,465 | B2 * | 10/2005 | Dieck et al. ................. 606/157 |
| 7,066,904 | B2 * | 6/2006 | Rosenthal et al. ...... 604/103.08 |
| 2001/0046518 | A1 * | 11/2001 | Sawhney .................... 424/486 |
| 2002/0165337 | A1 * | 11/2002 | Wallace et al. ............... 528/373 |
| 2002/0169473 | A1 * | 11/2002 | Sepetka et al. .............. 606/200 |
| 2002/0183783 | A1 | 12/2002 | Shadduck |
| 2004/0098023 | A1 * | 5/2004 | Lee et al. .................... 606/200 |
| 2004/0098028 | A1 * | 5/2004 | Martinez .................... 606/200 |
| 2005/0090856 | A1 | 4/2005 | Porter |

FOREIGN PATENT DOCUMENTS

| | | |
|---|---|---|
| WO | WO 02/089865 | 11/2002 |
| WO | WO 02/098272 | 12/2002 |
| WO | WO 03/015640 | 2/2003 |
| WO | WO 2004/045425 | 6/2004 |

OTHER PUBLICATIONS

PCT Written Opinion of the International Search Authority for PCT/US2004/033423, Applicant: Scimed Life Systems, Inc., Form PCT/ISA/237, dated Feb. 24, 2005 (5 pages).

PCT International Search Report for PCT/US2004/033329, Applicant: Scimed Life Systems, Inc., Forms PCT/ISA/210 and 220, dated Feb. 23, 2005 (8 pages).

PCT Written Opinion of the International Search Authority for PCT/US2004/033329, Applicant: Scimed Life Systems, Inc., Form PCT/ISA/237, dated Feb. 23, 2005 (6 pages).

Office Action dated May 8, 2006 for related U.S. Appl. No. 10/694,927, filed Oct. 27, 2003; Inventor Stephen C. Porter. (9 pages).

Amendment and Response to Office Action dated May 8, 2006, submitted on Aug. 7, 2006, for related U.S. Appl. No. 10/694,927, filed Oct. 27, 2003; Inventor Stephen C. Porter. (7 pages).

Final Office Action dated Oct. 17, 2006 for related U.S. Appl. No. 10/694,927, filed Oct. 27, 2003; Inventor Stephen C. Porter. (6 pages).

Amendment and Response to Final Office Action dated Oct. 17, 2006, submitted on Jan. 12, 2007, for related U.S. Appl. No. 10/694,927, filed Oct. 27, 2003; Inventor Stephen C. Porter. (11 pages).

Office Action dated Feb. 23, 2007 for related U.S. Appl. No. 10/694,927, filed Oct. 27, 2003; Inventor Stephen C. Porter. (8 pages).

Amendment and Response to Office Action dated Feb. 23, 2007, submitted on May 23, 2007, for related U.S. Appl. No. 10/694,927, filed Oct. 27, 2003; Inventor Stephen C. Porter. (7 pages).

Final Office Action dated Aug. 10, 2007 for related U.S. Appl. No. 10/694,927, filed Oct. 27, 2003; Inventor Stephen C. Porter. (6 pages).

* cited by examiner

VASO-OCCLUSIVE DEVICES WITH IN-SITU STIFFENING ELEMENTS

FIELD OF INVENTION

The invention pertains to medical devices, and more particularly to vaso-occlusive devices with in-situ stiffening elements to assist the devices to retain their deployed shape.

BACKGROUND

In many clinical situations, blood vessels are occluded for a variety of purposes, such as to control bleeding, to prevent blood supply to tumors, and to block blood flow within an aneurysm, arteriovenous malformation, or arteriovenous fistula.

Embolization of blood vessels is particularly useful in treating aneurysms. Aneurysms are abnormal blood filled dilations of a blood vessel wall, which may rupture causing significant bleeding. For the cases of intracranial aneurysms, the significant bleeding may lead to damage to surrounding brain tissue or death. Intracranial aneurysms may be difficult to treat when they are formed in remote cerebral blood vessels, which are very difficult to access. If left untreated, hemodynamic forces of normal pulsatile blood flow can rupture fragile tissue in the area of the aneurysm causing a stroke.

Vaso-occlusive devices have been used in the treatment of aneurysms. Vaso-occlusive devices are surgical implants placed within blood vessels or vascular cavities, typically by using a catheter as a conduit, to arrest blood flow, form a thrombus and occlude the site. For instance, a stroke or other such vascular occurrence may be treated by placing a vaso-occlusive device proximal of the site to block the flow of blood to the site and alleviate the leakage. An aneurysm may similarly be treated by introducing one or more vaso-occlusive devices through the neck of the aneurysm. The placement of the vaso-occlusive device(s) helps cause a mass to form in the aneurismal sac and alleviate the potential for growth of the aneurysm and its subsequent rupture. Other diseases, such as tumors, may often be treated by occluding the blood flow to the tumor.

There are a variety of known vaso-occlusive devices suitable for creating an embolic obstruction for therapeutic purposes. One such device is found in U.S. Pat. No. 4,994,069, to Ritchart et al. That patent describes a vaso-occlusive coil that assumes a linear helical configuration when stretched and a folded convoluted configuration when relaxed. The coil has a stretched configuration when placed in a catheter, which is used in placement of the coil at the desired site, and assumes the convoluted configuration when the coil is ejected from the catheter and the coil relaxes. Ritchart et al. describes a variety of shapes, including "flower" shapes and double vortices. A random shape is described as well.

Vaso-occlusive coils having complex, three-dimensional structures in a relaxed configuration are described in U.S. Pat. No. 6,322,576B1 to Wallace et al. The coils may be deployed in the approximate shape of a sphere, an ovoid, a clover, a box-like structure or other distorted spherical shape. The patent also describes methods of winding the anatomically shaped vaso-occlusive device into appropriately shaped forms and annealing them to form various devices.

Vaso-occlusive coils having little or no inherent secondary shape have also been described. For instance, U.S. Pat. Nos. 5,690,666 and 5,826,587 both by Berenstein et al. describe coils having little or no shape after introduction into the vascular space.

In accordance with one aspect of the invention, a vaso-occlusive device having an internal active element with in-situ stiffening capability is provided. In one embodiment, the vaso-occlusive device includes a coil, with the active element disposed within a lumen of the coil. The active element can have any of a number of shapes, such as, by way of non-limiting examples, an elongate shape, a form of a sphere, a cone, a plate, a mesh, or some other customized shape. By way of a further non-limiting example, the active element can be made from an expansive material, such as a hydrogel, that causes the active element to expand when placed in a body. In such an embodiment, the expanded active element imparts a radial stress within the coil to thereby stiffen and stabilize at least a portion of the coil in-situ.

One problem associated with existing vaso-occlusive devices is that they may not have a sufficient strength or stiffness to retain their shape after they are delivered into an aneurysm. When the above-mentioned vaso-occlusive devices are placed within an aneurysm, they tend to induce a formation of a thrombi for occlusion of the aneurysm. However, with time and the influence of hemodynamic forces and thrombolytic processes, the delivered vaso-occlusive devices may move or change shape due to their relatively low stiffness or through the process of seeking a minimally energetic morphology. As a result, the delivered vaso-occlusive devices may move out of the position or shape in which they were originally placed. In some cases, the delivered vaso-occlusive devices may even dislodge out of the sack of an aneurysm.

SUMMARY OF THE INVENTION

In accordance with one aspect of the invention, a vaso-occlusive device having an internal active element with in-situ stiffening capability is provided. In one embodiment, the vaso-occlusive device includes a coil, with the active element disposed within a lumen of the coil. The active element can have any of a number of shapes, such as, by way of non-limiting examples, an elongate shape, a form of a sphere, a cone, a plate, a mesh, or some other customized shape. By way of a further non-limiting example, the active element can be made from an expansive material, such as a hydrogel, that causes the active element to expand when placed in a body. In such an embodiment, the expanded active element imparts a radial stress within the coil to thereby stiffen and stabilize the shape of at least a portion of the coil in-situ.

Alternatively, the active element can be made from a material that causes the active element to contract when placed in a body. In such an embodiment, the active element may be anchored or secured to the coil at two points along a length of the coil. When the active element contracts, it compresses the coil between the two points of attachment, to thereby stiffen and stabilize the shape of at least a portion of the coil in-situ.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals, and in which.

DETAILED DESCRIPTION OF PREFERRED EMBODIMENTS

Delivery of a Bioactive Agent

Figure 1:
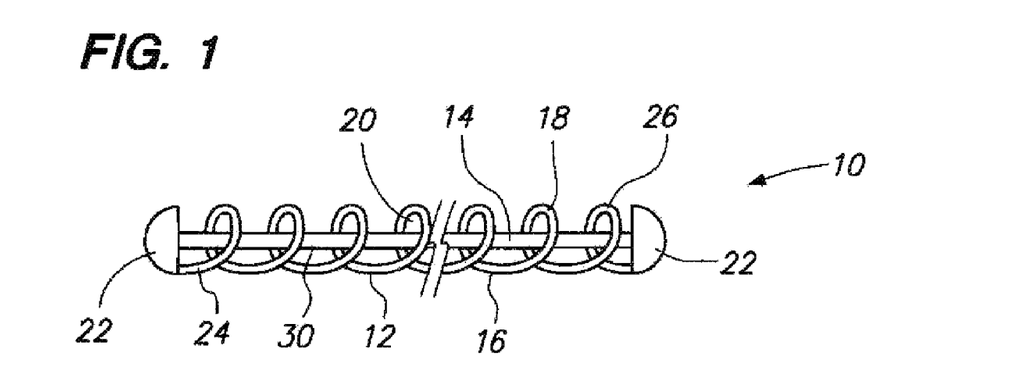
FIG. 1 is a side view of a vaso-occlusive device in accordance with one embodiment, including an agent carrier disposed within a lumen of a coil.

In accordance with one aspect of the invention, the vasso-occlusive device 10 of FIG. 1 is provided with an agent carrier 14 carried by the coil 12. The coil 12 is made from a linear element 16, such as a wire, which preferably has a circular cross-sectional shape. In alternative embodiments, the linear element 16 of the coil 12 may have a rectangular, triangular, other geometric cross-section, or an irregular shaped cross-section. The coil 12 includes one or more loops or windings 18 formed by the linear element 16. The loops 18 define a central lumen 20 in which the agent carrier 14 is placed. In the illustrated embodiment, the vaso-occlusive device 10 has an overall diameter or cross-section which is preferably in the range of 0.010 to 0.023 inches. However, the vaso-occlusive device 10 may have other diameters and/or cross-sections, as well.

The vaso-occlusive device 10 may optionally include one or more end caps 22 secured to a first end 24 or to a first and a second end 26 of the coil 12.

The coil 12 may have an open or closed (e.g., FIGS. 9-11) pitch. The coil 12 shown in FIG. 1 may be constructed by wrapping the linear element 16, such as a wire, around a mandrel, stylet, or other shaping element. The coil 12 may optionally be heat treated, as known to one skilled in the art. It should be noted that the formation of vaso-occlusive devices having a helical coil shape is well known in the art, and need not be described in further detail.

The coil 12 may be made of a variety of materials, such as metals or polymers. Suitable metals and alloys for the coil 12 may include the Platinum Group metals, especially platinum, rhodium, palladium, rhenium, as well as tungsten, gold, tantalum, and alloys of these metals. These metals have significant radiopacity and their alloys may be tailored to accomplish an appropriate blend of flexibility and stiffness. These metals are also largely biologically inert. The coil 12 may also be formed from stainless steels if some sacrifice of radiopacity may be tolerated. Other materials that may be used may include "super-elastic alloys," such as nickel/titanium ("Nitinol") alloys, copper/zinc alloys, or nickel/aluminum alloys. Exemplary alloys that may be used are described in U.S. Pat. Nos. 3,174,851, 3,351,463, and 3,753,700. If Nitinol is used, the diameter of the coil 12 may be significantly smaller than that of a coil 12 made from relatively more ductile platinum or platinum/tungsten alloy.

Examples of polymers that may be used for construction of the coil 12 includes polydienes, polyalkenes, polystyrenes, polyoxides, polycarbonates, polyesters, polyanhydrides, polyurethanes, polyamides, polyimides, polyacrylics, polymethacrylics, polyacetals, and vinyl polymers. The coil 12 can alternatively be made of radiolucent fibers or polymers, such as Dacron (polyester), polyglycolic acid, polylactic acid, fluoropolymers (polytetrafluoroethylene), Nylon (polyamide), and/or silk.

If the coil 12 is not made from a radiopaque material, the coil 12 may be coated, mixed, or filled with radiopaque materials such as metals (e.g. tantalum, gold, tungsten or platinum), barium sulfate, bismuth oxide, bismuth subcarbonate, zirconium oxide, and the like. Alternatively, continuous or discrete radiopaque markers may be incorporated within or affixed to the coil 12.

As shown in FIG. 1, the agent carrier 14 includes one or more axially oriented elements 30 having a substantially rectilinear or a curvilinear (less than 360°) configuration along a length of the vaso-occlusive device 10. In the case of a more complex coil shape, the active element could mirror the shape of the coil. The axially oriented element 30 is located within the lumen 20 of the coil 12 and is secured to the ends 24 and 26 or the end caps 22 of the coil 12. The securing may be accomplished by an anchor or a suitable adhesive, such as ultraviolet-curable adhesives, silicones, cyanoacrylates, or epoxies. Alternatively, the axially oriented element 30 can be secured to the coil 12 by chemical bonding between reactive groups on the axially oriented element 30 and the coil 12, solvent bonding, fusing both materials so that they melt together, or temporarily melting the surface of the coil 12 to embed part of the axially oriented element 30.

An advantage of securing the axially oriented element 30 to both ends 24 and 26 of the coil 12 is that the axially oriented element 30 can function as a stretch-resistant member, which prevents the first end 24 of the coil 12 from being pulled too far from the second end 26. The axially oriented element 30 can also be pre-stretched before it is secured to the ends of the coil 12, to thereby provide some degree of compression within the coil 12. Examples of stretch-resistant members are described in U.S. Pat. Nos. 6,193,728, 6,013,084, 6,004,338, 5,853,418, 5,833,705, 5,582,619.

In alternative embodiments, instead of securing to both ends of the coil 12, the axially oriented element 30 can be secured to the coil 12 at one of the ends 24 and 26 of the coil 12 or at one or more points along a length of the coil 12 by a suitable adhesive or by wrapping around one or more windings 18 of the coil 12. In another embodiment, the axially oriented element 30 is not secured to the coil 12, but is simply disposed within the lumen 20 of the coil 12, or is coupled to the coil 10 by a surface friction, in which case, the surface of the axially oriented element 30 may be textured to improve the coupling force between the axially oriented element 30 and the coil 12.

The agent carrier 14 preferably has a cross-sectional dimension such that the overall flexibility of the vaso-occlusive device 10 is not significantly impacted. In one embodiment, the cross-sectional dimension of the agent carrier 14 is approximately 0.002 inch less than the internal diameter of the coil 12. However any diameter smaller than the coil internal diameter may also be used. If the agent carrier 14 is also used as a stretch-resistant member, the agent carrier 14 should have a minimum cross-sectional dimension such that the agent carrier 14 can have enough strength to provide some degree of tensile resistance to a stretching of the coil 12.

The agent carrier 14 includes a bioactive material or agent, such as a thrombogenic or a therapeutic agent, that induces a tissue reaction when placed within a body. Particularly, the agent carrier 14 is made from a bioactive material or agent that is absorbable or biodegradable. When the vaso-occlusive device 10 is placed in a body, the agent carrier 14 dissolves and releases the agent to its surrounding environment. Alternatively, the agent carrier 14 can be made from a non-biodegradable material, in which case, a coating that comprises a bioactive agent is then deposited on a surface of the agent carrier 14. When the vaso-occlusive device 10 is placed within an aneurysm, a body temperature and/or a reaction with a bodily fluid causes the coating to degrade or dissolve, thereby releasing the bioactive agent.

Notably, the bioactive agent may be incorporated within the agent carrier, e.g., in a cavity, or dispersed within the material comprising the agent carrier itself, such material being either absorbable or non-absorbable.

Preferably, the bioactive agent is a type which elicits a tissue reaction that leads to rapid in-growth of fibro-cellular tissue, thereby stabilizing the occlusion of the aneurysm without compromising blood flow in the native vasculature. An advantage of placing the agent carrier 14 within the lumen 20 of the coil 12 is that an exterior of the coil 12 is unaffected by the bioactive material during delivery of the coil 12. That is, the bioactive material would not increase a friction between the coil 12 and a delivery tool, and would not cause the coil 12 to be adhered to the delivery tool or to a packaging.

Examples of materials that can be included in the agent carrier 14 include homopolymers or copolymers comprising in part: polyesters, acrylics, polyethers, polysiloxanes, polyurethanes, polycarbonates, and other biocompatible polymers. Biodegradable or absorbable materials may also be used in the agent carrier and/or as the bioactive agent and include, but are not limited to, synthetic polymers, polysaccharides, and proteins. Suitable polymers may include, for example, polyglycolic acid, polylactic acid, polycaprolactone, polyhydroxyalkanoates (such as polyhydroxybutyrate and polyhydroxyvalerate), polydioxanone, poly(trimethylene carbonate), polyanhydrides, poly(g-ethyl glutamate), poly(DTH iminocarbonate), poly(bisphenol A iminocarbonate), polyarylates, polyamino acids and copolymers or mixtures thereof.

In addition, or alternatively, proteins may be used, such as collagen, elastin, caesin, fibrin, fibrinogen, fibronectin, vitronectin, laminin, silk, and/or gelatin. In addition or alternatively, polysaccharides may be used, such as chitin, chitosan, cellulose, alginate, hyaluronic acid, and chondroitin sulfate. Many of these materials are commercially available. Fibrin-containing compositions are commercially available, for example from Baxter Healthcare. Collagen-containing compositions are commercially available, for example, from Cohesion Technologies, Inc., of Palo Alto, Calif. Fibrinogen-containing compositions are described, for example, in U.S. Pat. Nos. 6,168,788 and 5,290,552. As will be readily apparent, absorbable materials may be used alone or in any combination with each other. The absorbable material may be a mono-filament or multi-filament strands or a tube.

The materials that comprise the carrier can themselves be bioactive. These materials in their unaltered or in a degraded form may stimulate a biological reaction that ultimately results in the formation of fibro-cellular tissues. For example, certain polymers such as bioabsorbable polymers or certain polyesters can illicit an inflammatory reaction; certain proteins such as fibrinogen or collagen can illicit a thrombogenic reaction; and other proteins such as silk can illicit an immune response.

Other examples of bioactive materials that can be included in the agent carrier 14 include cytokines; extracellular matrix molecules (e.g., collagen, fibrin, or decellularized animal tissues); matrix metalloproteinase inhibitors; trace metals (e.g., copper); other molecules that may stabilize thrombus formation or inhibit clot lysis (e.g., proteins, including Factor XIII, $\alpha_2$-antiplasmin, plasminogen activator inhibitor-1 (PAI-1), and the like); and their functional fragments (e.g., the P1 or P2 epitopes of fibrin). Examples of cytokines that may be used alone or in combination with other compounds may include basic fibroblast growth factor (bFGF), platelet derived growth factor (PDGF), vascular endothelial growth factor (VEGF), transforming growth factor beta (TGF-β), and the like. Cytokines, extracellular matrix molecules, matrix metalloproteinase inhibitors, and thrombus stabilizing molecules are commercially available from several vendors, such as Genzyme (Framingham, Mass.), Genentech (South San Francisco, Calif.), Amgen (Thousand Oaks, Calif.), R&D Systems, and Immunex (Seattle, Wash.).

Additionally, bioactive polypeptides that may be synthesized recombinantly as the sequence of many of these molecules are also available, for example, from the GenBank database. Thus, the agent carrier 14 may include use of DNA or RNA encoded bioactive molecules. Furthermore, molecules having similar biological activity as wild-type or purified cytokines, extracellular matrix molecules, matrix metalloproteinase inhibitors, thrombus-stabilizing proteins (e.g., recombinantly produced or mutants thereof), and nucleic acid encoding these molecules may also be used. The amount and concentration of the bioactive materials that may be included in the composition of the agent carrier 14 may vary depending upon the specific application. It will be understood that any combination of materials, concentration, and/or dosage may be used, so long as it is not harmful to the subject.

The structural materials that comprise the carrier can themselves be the bioactive agent. These materials in their unaltered or in a degraded form may stimulate a biological reaction that ultimately results in the formation of fibro-cellular tissues. For example, certain polymers such as bioabsorbable polymers or certain polyesters can illicit an inflammatory reaction; certain proteins such as fibrinogen or collagen can illicit a thrombogenic reaction; and other proteins such as silk can illicit an immune response.

In alternative embodiments, instead of being made from a bioactive material, the agent carrier 14 is made from a material that adheres or absorbs a bioactive agent. For examples, the agent carrier 14 may include one or more polymer filaments, a sponge, a cloth, a hydrogel, or other materials that are capable of absorbing or adhering a bioactive agent. In this case, the agent carrier 14 is used to deliver the bioactive agent, which will diffuse out of the agent carrier 14 into the surroundings when placed in an aneurysm.

The bioactive agent may also be disposed within the carrier, e.g., wherein the carrier has a sealed reservoir containing the agent, or wherein the agent is dispersed within the material comprising the container. In such embodiments, the agent will diffuse out of the carrier. The selected agent preferably elicits a tissue reaction that leads to rapid in-growth of fibrocellular tissue, thereby stabilizing the occlusion of the aneurysm. The agent may include any of the materials described previously. The agent may also include drugs, proteins, cells, genetic modifiers, inflammatory agents, immuno-agonistic agents (e.g. Freunds adjuvant or squalene), clot stabilizer, clot activators (e.g. thrombin or Factor XIII), cellular materials (e.g. concentrated blood products, fibroblasts, smooth muscle cells, progenitor cells, genetically engineered cells that secrete a particular bioactive protein), viral vectors, or plasmids.

In-Situ Stiffening of Vaso-Occlusive Device

Figure 2:
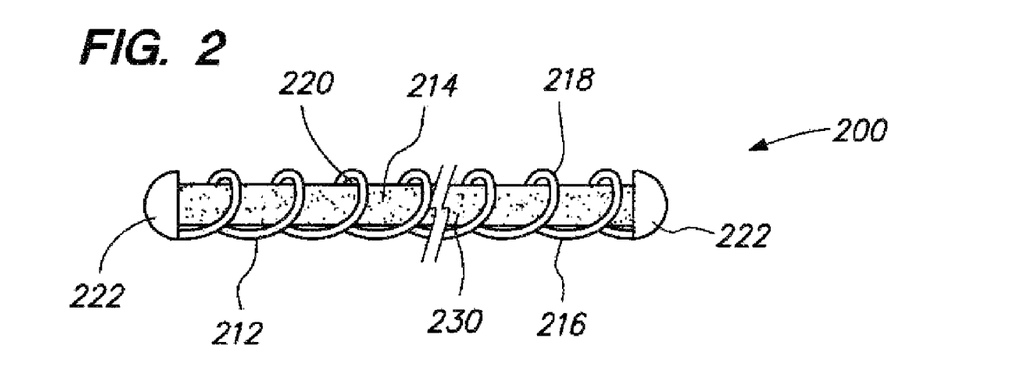
FIG. 2 is a side view of a vaso-occlusive device in accordance with another embodiment, including an active element disposed within a lumen of a coil.

In accordance with another aspect of the invention, the vasso-occlusive device 200 of FIG. 2 is provided with an active element 214 configured to provide in-situ stiffening of the coil 200. The coil 212 is made from a linear element 216, such as a wire, which preferably has a circular cross-sectional shape. Alternatively, the linear element 216 of the coil 212 may have a rectangular, triangular, other geometric cross-section, or an irregular shaped cross-section.

The coil 212 includes one or more loops or windings 218 formed by the linear element 216. The loops 218 define a central lumen 220 in which the active element 214 is placed. Any of the materials described previously with reference to the coil 12 is also suitable for construction of the coil 212. In the illustrated embodiment, the vaso-occlusive device 200 has an overall diameter or cross-section which is preferably in the range of 0.010 to 0.023 inches. However, the vaso-occlusive device 200 may have other diameters and/or cross-sections, as well. The vaso-occlusive device 200 may optionally include one or more end caps 222 secured to a first end 224 and/or a second end 226 of the coil 212.

As shown in FIG. 2, the active element 214 includes an axially oriented element 230 having a substantially rectilinear or a curvilinear (less than 360°) configuration along a length of the vaso-occlusive device 200. Again, in the case of more complex coil shapes, the active element could mirror the shape of the coil. The axially oriented element 30 is located within the lumen 220 of the coil 212 and is secured to the ends 224 and 226 or the end caps 222 of the coil 212. The securing may be accomplished by any of the methods described previously.

In alternative embodiments, instead of securing to both ends 224 and 226 of the coil 212, the axially oriented element 230 can be secured to the coil 212 at one of the ends 224 and 226 of the coil 212 or at one or more points along a length of the coil 212 by a suitable adhesive or by wrapping around one or more windings 218 of the coil 212. Furthermore, in another embodiment, the axially oriented element 230 is not secured to the coil 212. In this case, the axially oriented element 230 is simply disposed within the lumen 220 of the coil 212, or is coupled to the coil 210 by a surface friction, in which case, the surface of the axially oriented element 230 may be textured to improve the coupling force between the axially oriented element 230 and the coil 212.

Figure 3:
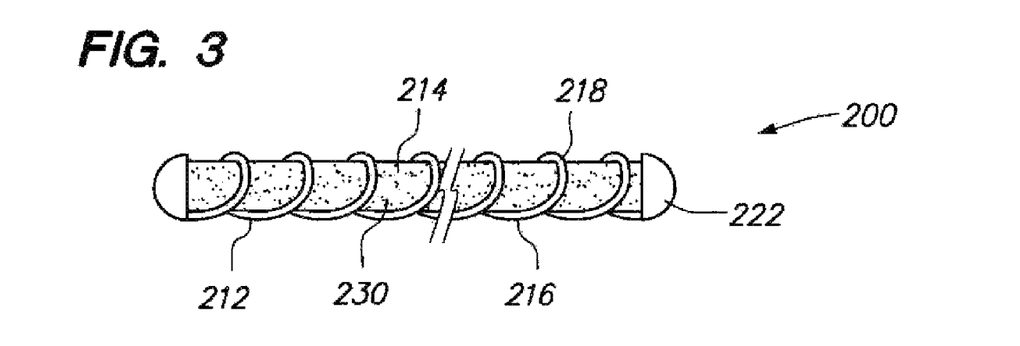
FIG. 3 is a side view of the vaso-occlusive device of FIG. 2, showing the active element having an expanded configuration.

The active element 214 is configured to undergo a reaction that changes a structural characteristic of the vaso-occlusive device 200 when placed in a body cavity. In one embodiment, the active element 214 includes an expansible material, which will expand in size when placed in an aqueous environment within a living mammal. In this case, the cross-section of the active element 214 is configured such that it can expand to a size which is slightly larger than the internal diameter (or the lumen 220) of the coil 212 (FIG. 3). In one embodiment, the cross-sectional dimension of the active member 214 is configured such that its swollen cross-sectional dimension is at least equal to 100%-500%, and more particularly, between 110%-200%, of the internal diameter of the coil 212. The expanded material imparts a radial stress within the coil 212 to thereby stiffen and stabilize the coil 212 in-situ.

An example of the expansible material that can be used for construction of the active element 214 is a hydrogel, which is capable of absorbing a desired amount of aqueous fluid. Examples of hydrogels include gels formed from homopolymers, copolymers, and/or network polymers containing: polyethylene glycol, polypropylene glycol, polyvinyl alcohol, polyvinylpyrrolidone, polyacrylates, polymethacrylates, polyacrylamides, polyethyloxazoline, polysaccharides, mucopolysaccharides, polyaminoacids, carboxy alkyl celluloses, partially oxidized cellulose, hyaluronic acid, dextran, heparin sulfate, chondroitin sulfate, heparin, agar, starch, alginate, fibronectin, gelatin, collagen, fibrin, pectins, albumin, polyesters of .alpha.-hydroxy acids including polyglycolic acid, poly-DL-lactic, poly-L-lactic acid, polylactones, polyanhydrides, polyorthoesters, polydioxanone, polycaprolactones, poly(delta-valerolactone), poly(gamma-butyrolactone), and combinations thereof. The gel may further comprise a chemical cross-linking agent having two or more reactive groups in order to form chemical bridges between two or more polymeric molecules. Examples of such cross-linking agents include diacrylates, oligoacrylates, dimethacrylates, oligomethacrylates, divinyl ethers, certain cations, and combinations thereof.

The active element 214 can also include a radiopaque material mixed or coated with the hydrogel, or alternatively, include a radiopaque marker secured to the active element 214.

Other expansive materials that respond to changes in moisture, ionic strength, temperature, pH, or materials that selectively absorb blood borne substances (e.g. silicones or other polymers which absorb lipids) may also be used. The rate at which the active element 214 expands may be customized, such as by changing a composition of the active element 214, so that placement and repositioning of the coil 212 may be performed within a period after it has been delivered to a site. The rate at which the active element 214 expands may also be customized or by varying a spacing between the pitch of the coil 212, thereby controlling the amount of bodily fluid that flows into the lumen 220 of the coil 212. The rate may also be controlled by a coating that may be soluble or insoluble which, in either case, limits diffusion of water into the active element.

In another embodiment, the active element 214 is made from a material that undergoes contraction due to an environmental stimuli, such as moisture, ionic strength, pH temperature. In this case, the active element 214 is secured to the coil 212 at two points along a length of the coil 212. For example, the active element 214 can be secured to the ends 224 and 226 of the coil 212 using any of the methods described previously. Alternatively, the active element 214 can also be secured to the coil 212 along its length by an adhesive or by wrapping around the loops 218 of the coil 212. When the active element 214 is placed inside a body, it reacts with a stimuli, such as blood or other bodily fluids, and undergoes contraction. Contraction of the active element 214 induces a compressive load on the coil 212 (i.e., the active element 214 compresses the coil 212 between the two points of attachment), which in turn stiffens and stabilizes the coil 212 in-situ.

Contraction of the active element may be achieved, by way of example, by localized injection of a warm fluid or an ionic solution, provided that the material transition is irreversible. Alternatively, the active element may be pre-tensioned, wherein prior to use, the device is conditioned with a solvent (e.g., an aqueous ionic solution or polar organic solvent) to cause initial expansion of the element prior to placement inside a body. Once placed in the body, contact with blood causes the solvent to diffuse out of the active element, further causing it to contract.

Examples of materials that undergoes contraction due to an environmental stimuli includes shape memory alloys and polymers, such as Nitinol™ or polyurethanes and poly(norbornene), which contract (or expand) with changes in temperature. Other, temperature-sensitive contracting materials include protein fibers that undergo thermally induced phase transitions or denaturation at or near body temperature, and thermoresponsive hydrogels, which include polymer gels swollen by aqueous solutions which change volume in response to thermally induced molecular motions that alter the balance of hydrophilic/hydrophobic interactions between the polymer chains and the surrounding aqueous environment. Examples of such hydrogels include ones containing n-isopropyl, acrylamide, chitosan, hyaluronic acid, or poly (ethylene oxide-co-propylene oxide). Examples of materials that contract in response to changes in pH and/or ionic strength include polyelectrolyte hydrogels, which are polymer gels swollen by aqueous solutions which change volume in response to electrostatic interactions between polymer chains and ions in the surrounding aqueous environment. Examples of such hydrogels include ones containing acrylic acid, n-isopropyl acrylamide, amino acids, carboxyl methacrylate, chitosan or xanthan. Protein fibers that undergo pH induced phase transitions or denaturation at or near body pH may also be suitable for use as a contracting agent, as would polymer gels comprising a biocompatible polymer swollen with a non-aqueous solvent that will diffuse out of the gel upon contact with water (or blood), such as silicones, urethanes, acrylics and polyesters.

It should be noted that although the vaso-occlusive device 10 has been described as having an agent delivery capability, and the vaso-occlusive device 200 has been described as having an in-situ stiffening capability, the scope of the invention should not be so limited. In an alternative embodiment, a vaso-occlusive device can be configured both to be stiffened in-situ and to deliver a bioactive agent. For example, the vaso-occlusive device 200 configured to be stiffened in-situ can also carry a bioactive agent that causes a tissue reaction when delivered in a body.

In the previously described embodiments, the agent carrier 14 and the active element 214 have a substantially rectilinear or curvilinear (less than 360°) shape. However, the agent carrier 14 and the active element 214 are not limited to those described previously, and can have other shapes or configurations in alternative embodiments so long as they are located substantially within the central lumen of the coil.

Figure 4:
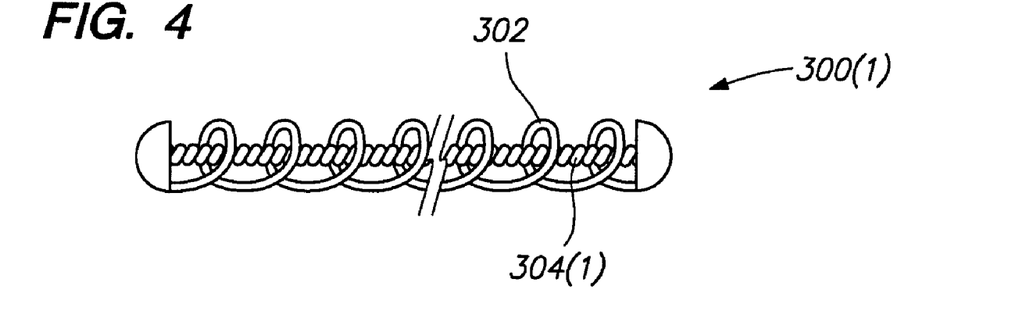
FIGS. 4-6 are side views of embodiments of vaso-occlusive devices.
Figure 5:
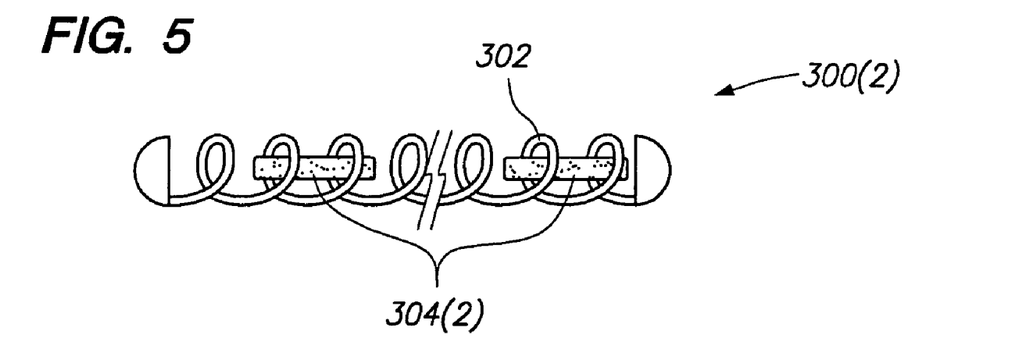
Figure 6:
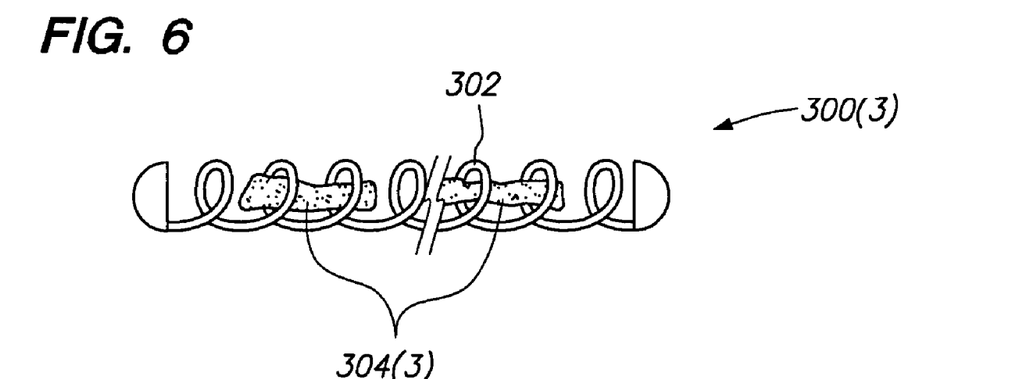

FIGS. 4-6 each shows a vaso-occlusive device 300 having a coil 302 and an internal element 304 in accordance with alternative embodiments of the present invention. The coil 302 in these figures represents the coil 12 or the coil 212 described previously, and the internal element 304 represents the agent carrier 14 or the active element 214 described previously.

FIG. 4 shows a vaso-occlusive device 300(1) that includes a coil 302 and an internal element 304(1) having a shape of a coil. As similarly discussed previously, the internal element 304(1) may be secured to one or both ends of the coil 302, secured to the coil 302 at one or more points along a length of the coil 302, or coupled to the coil 302 by a surface friction.

FIG. 5 shows another vaso-occlusive device 300(2) that includes a coil 302 and one or more internal elements 304(2). In this case, the internal element 304(2) does not extend approximately from one end to the other end of the coil 302. Instead, the internal element 304(2) only extends along a portion of the length of the coil 302. In the illustrated embodiment, the internal element 304(2) has a shape of a cylinder. However, the internal element 304(2) can also have other shapes or configurations. For examples, the internal element 304(2) can be in a form of a sphere, a cone, a plate, a mesh, or other customized shapes. FIG. 6 shows a vaso-occlusive device 300(3) that includes an internal element 304(3) having a random shape.

The vaso-occlusive devices shown in the above-described embodiments generally have a substantially rectilinear (straight) or a curvilinear (slightly curved, i.e. having less than 360° spiral) relaxed configurations. Such devices may assume folded or bent configurations when they are subjected to an external force (e.g., compressive forces generated when they are pushed against an object, such as the wall of an aneurysm). The devices may also assume a variety of secondary shapes or relaxed configurations. The space-filling capacity of these vaso-occlusive devices is inherent within the secondary relaxed shape of these devices.

FIGS. 7-13 illustrate various vaso-occlusive devices 400 that include a coil 402 having a primary shape and a secondary shape. These shapes are simply indicative of the various secondary shapes that may be used, and other shapes may be used as well. While not always shown, the devices 400 illustrated in FIGS. 7-13 are each provided with an internal element 304, which can be the agent carrier 14 or the active element 214, as discussed previously.

Figure 7:
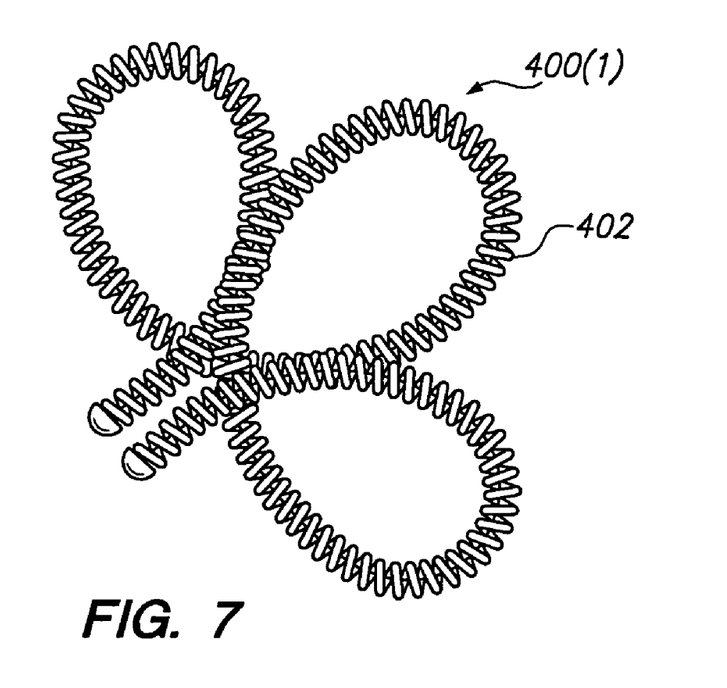
FIGS. 7-13 show embodiments of vaso-occlusive devices having secondary shapes.
Figure 8:
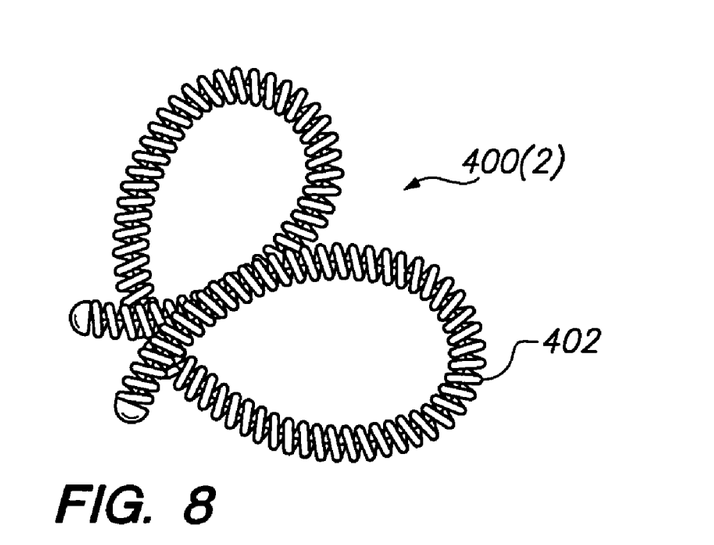
Figure 9:
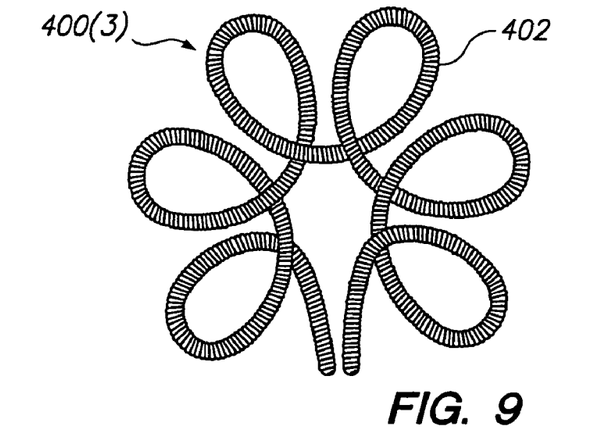
Figure 10:
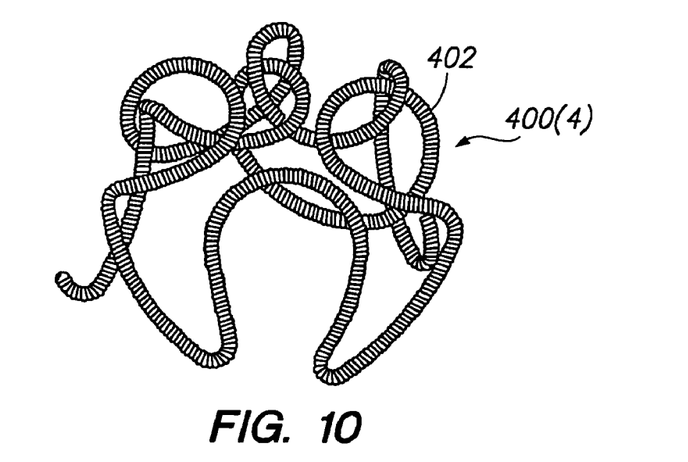
Figure 11:
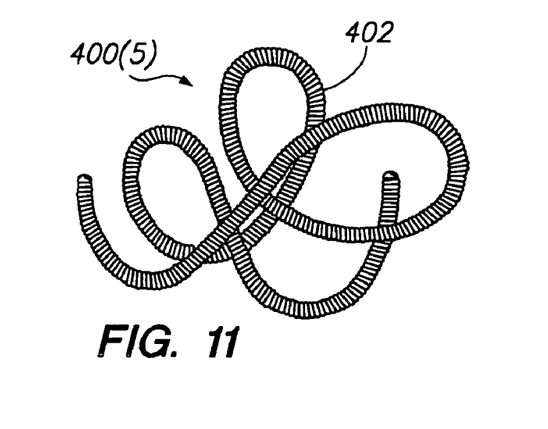
Figure 12:
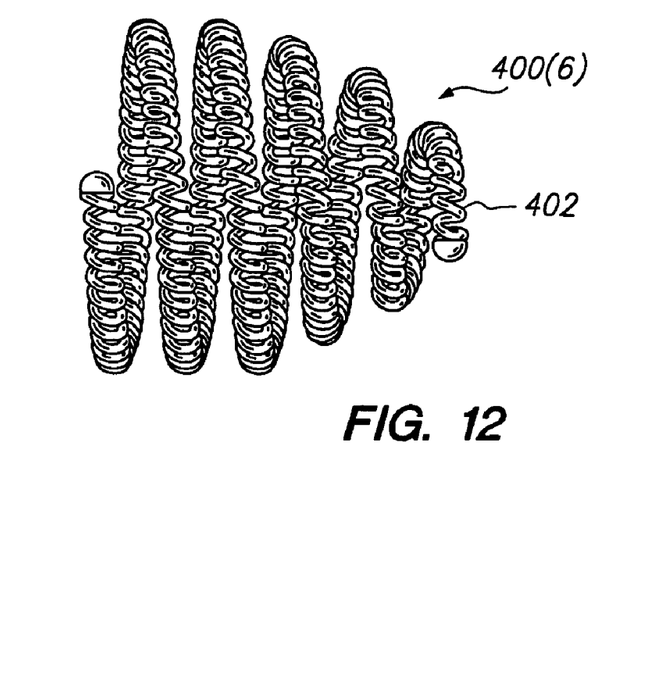
Figure 13:
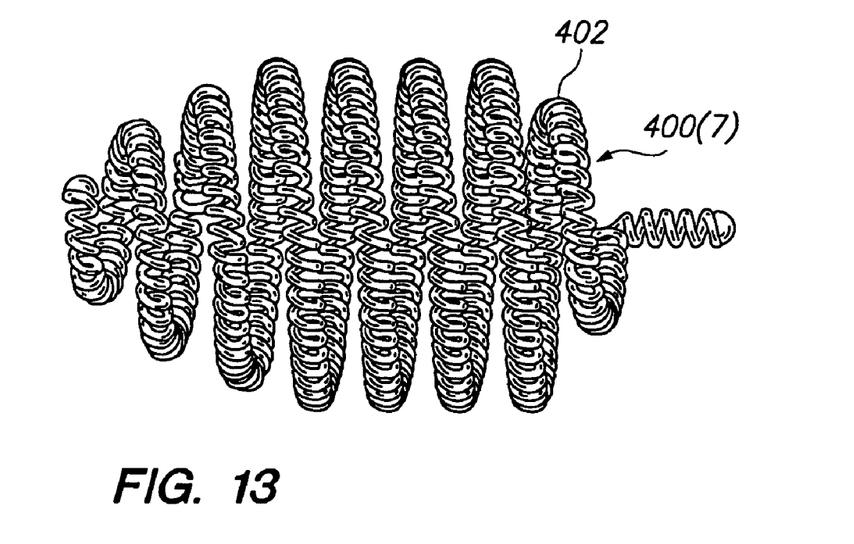

FIG. 7 depicts a device 400(1) having a secondary shape of a clover leaf. FIG. 8 depicts a device 400(2) having a secondary shape of a twisted figure-8. FIG. 9 depicts a device 400(3) having a flower-shaped secondary shape. FIG. 10 depicts a device 400(4) having a substantially spherical secondary shape. FIG. 11 illustrates a device 400(5) having a random secondary shape. FIG. 12 illustrates a device 400(6) having a secondary shape of a vortex. FIG. 13 illustrates a device 400(7) having a secondary shape of an ovoid. It should be noted that vaso-occlusive device 400 may also have other secondary shapes, and that it should not be limited to the examples illustrated previously. For example, the vaso-occlusive device 400 may be selectively sized to fill a particular aneurysm or body cavity.

To make a secondary shaped vaso-occlusive device 400, a coil (i.e., the coil 402) having a primary shape that is substantially rectilinear or curvilinear may be wrapped around a mandrel or other shaping element to form a secondary shape. The coil 402 may be heat treated to shape the coil 402 into the secondary shape. Stable coil designs, and methods of making them, are described in U.S. Pat. No. 6,322,576B1 to Wallace et al. It should be noted that forming vaso-occlusive devices into secondary shapes is well known in the art.

Figure 14:
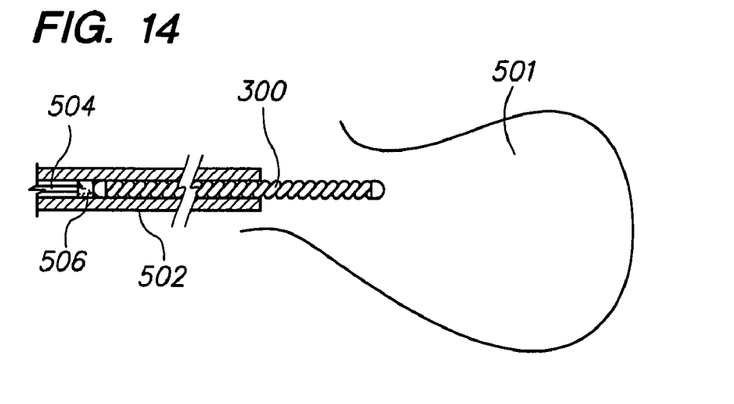
FIG. 14 is a cross-sectional side view of an embodiment of a vaso-occlusive device being delivered using a delivery catheter, showing the coil of the vaso-occlusive device having a substantially rectilinear shape inside the delivery catheter.
Figure 15:
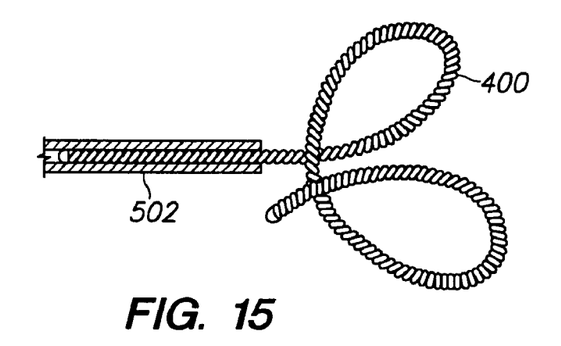
FIG. 15 is a cross-sectional side view of an embodiment of a vaso-occlusive device being delivered using a delivery catheter, showing the vaso-occlusive device changing from a stretched configuration to relaxed configuration as it exits from the delivery catheter.

A method of using the previously described vaso-occlusive devices (i.e., device 300) will now be discussed with reference to FIGS. 14 and 15. First, a delivery catheter 502 is inserted into the body of a patient. Typically, this would be through a femoral artery in the groin. Other entry sites sometimes chosen are found in the neck, for example, and are in general well known by physicians who practice these types of medical procedures. The delivery catheter 502, which may be a microcatheter or a sheath, may be positioned so that the distal tip 508 of the delivery catheter 502 is appropriately situated, e.g., within the mouth of the body cavity 501 to be treated. The insertion of the delivery catheter 502 may be facilitated by the use of a guidewire and/or a guiding catheter, as is known in the art. In addition, the movement of the catheter 502 may be monitored, for example, using fluoroscopy, ultrasound, and the like.

Once the delivery catheter 502 is in place, the vaso-occlusive device 300 is then inserted from the proximal end (not shown) of the delivery device 502, and into the lumen of the delivery device 502. This step is not necessary if the vaso-occlusive device 300 is already pre-loaded into the delivery catheter 502. Since the vaso-occlusive device 300 has no secondary shape, the vaso-occlusive device 300 would naturally assume a substantially rectilinear or a curvilinear configuration when disposed within the lumen of the delivery device 502, without being subjected to a substantial stress. For vaso-occlusive devices having secondary shapes, such as the vaso-occlusive devices 400 shown in FIGS. 7-13, they may be "bent" to a substantially linear shape while residing within the lumen of the delivery catheter 502, as illustrated in FIG. 15.

Referring back to FIG. 14, the vaso-occlusive device 300 is preferably advanced distally towards the distal end 508 of the delivery catheter 502 using a core wire or pusher member 504. A plunger 506 may be attached to the distal end of the wire 504 to advance the vaso-occlusive device 300. Alternatively, fluid pressure may also be used to advance the vaso-occlusive device 300 along the delivery catheter 502. The inner diameter of the delivery catheter 502 should be made large enough to advance the vaso-occlusive device 300. On the other hand, the inner diameter of the delivery catheter 502 should not be significantly larger than the overall cross-sectional dimension of the vaso-occlusive device 300 in order to avoid buckling and/or kinking the vaso-occlusive device 300 within the lumen of the delivery catheter 502.

Additional vaso-occlusive devices 300 may also be placed within the body cavity 501 by repeating the relevant steps discussed above. When a desired number of vaso-occlusive devices has been placed within the body cavity 501, the delivery catheter 502 may be withdrawn from the body cavity 501 and the patient's body. Once the vaso-occlusive devices are deployed in the body cavity 501, an embolic mass is formed therein to occlude the body cavity 501.

Figure 16:
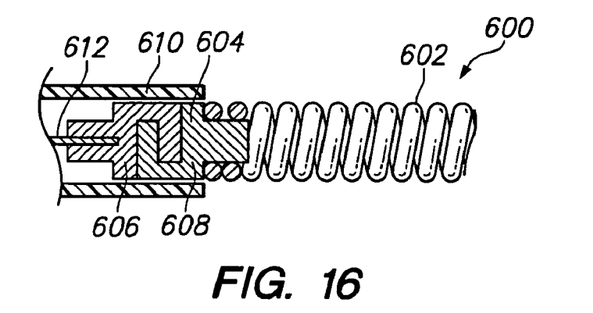
FIG. 16 is a side view of a portion of a delivery catheter from which a vaso-occlusive device is deployed and mechanically released.
Figure 17:
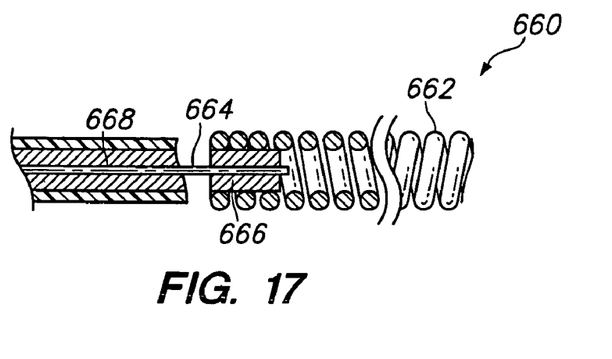
FIG. 17 is a side view of a portion of a delivery catheter from which a vaso-occlusive device is deployed and electrolytically released.

Other devices and methods for discharging shaped coils and linear coils into a body cavity may also be used. FIGS. 16 and 17 each shows a detachable device that can release a vaso-occlusive coil at a specifically chosen time and site.

FIG. 16 depicts an embodiment, generally designated 600, having a vaso-occlusive device 602 that may be deployed from a sheath or a catheter 610 through operation of a connective joint 604. The vaso-occlusive device 602 may be any of the devices depicted in FIGS. 1-13, i.e., including the agent carrier 14 or the active element 214 (not shown for clarity). Joint 604 has a clasp section 606 that may remain attached to a core wire 612 when the sheath or catheter body 610 is retracted proximally. Joint 604 also may include a second clasp section 608, carried on the proximal end of the vaso-occlusive device 602 and interlocking with clasp section 606 when the assembly is within the sheath 610. When the sheath 610 is withdrawn from about the assembly, the clasp sections may disengage, thereby detaching the vaso-occlusive device 602.

The vaso-occlusive devices described herein may also be detachable by an electrolytic joint or connection, such as described in U.S. Pat. Nos. 5,234,437, 5,250,071, 5,261,916, 5,304,195, 5,312,415, and 5,350,397.

FIG. 17 shows an embodiment, generally designated 660, having a vaso-occlusive device 662 that may be detached using a connective joint 664 that is susceptible to electrolysis. The vaso-occlusive device 662 may be any one of the devices depicted in FIGS. 1-13, and includes the agent carrier 14 or the active element 214 (not shown for clarity). Joint 664 may be made of a metal which, upon application of a suitable voltage to a core wire 668, may erode in the bloodstream, thereby releasing the vaso-occlusive device 662. The vaso-occlusive device 662 may be made of a metal that is more "noble" in the electromotive series than the joint 664. A return electrode (not shown) may be supplied to complete the circuit.

The region of core wire 668 proximal to the joint is insulated to focus the erosion at the joint. A bushing 666 may be used to connect the distal end of core wire 404 to the proximal end of the vaso-occlusive device 662. To deploy the vaso-occlusive device 662, the vaso-occlusive device 662 attached to the core wire 668 is first placed within a body cavity. An electric current is then applied to the core wire 668 to dissolve the connective joint 664, thereby detaching the vaso-occlusive device 662 from the core wire 668. It should be noted that methods of delivering vaso-occlusive devices by electrolytic disintegration of a core wire joint are well known in the art, and need not be described in further detail. The above described joint and similar joints are described in detail in U.S. Pat. No. 5,423,829, 6,165,178, and 5,984,929.

Although preferred embodiments of the invention are shown and described herein, it would be apparent to those skilled in the art that many changes and modifications may be made thereto without the departing from the scope of the invention, which is defined by the appended claims.

By way of one example, it will be readily apparent that the two main aspects of the invention disclosed and described herein—that of an occlusive device carrying an active element for providing in-situ stiffening of the device after its placement in a selected site in the vasculature, and that of an occlusive device including an agent carrier comprising (or otherwise carrying) a biological agent that elicits a biological reaction inside a body, may be combined in a single embodiment of the invention.

What is claimed:

1. A vaso-occlusive device, comprising:
a helically wound coil comprising a plurality of adjacent loops, each loop having an open interior region, the coil defining an axial lumen extending through the respective interior regions of the adjacent loops; and
a hydrogel member having a pre-deployment configuration carried entirely within the coil lumen with no portion of the pre-deployed hydrogel member located outside of the lumen, wherein the hydrogel member is configured to radially contract to a deployed configuration without application of a mechanical force after being placed in a body vasculature site to thereby cause the coil to substantially retain its shape when deployed in the body vasculature site.

2. A vaso-occlusive device, comprising:
a helically wound coil comprising a plurality of adjacent loops, each loop having an open interior region, the coil defining an axial lumen extending through the respective interior regions of the adjacent loops; and
an active element having a pre-deployment configuration carried entirely within the lumen with no portion of the pre-deployed active element located outside of the lumen, wherein the active element is configured to radially contract to a deployed configuration without application of a mechanical force after being placed in a body vasculature site to thereby cause the coil to substantially retain its shape when deployed in the body vasculature site.

3. The vaso-occlusive device of claim 2, wherein the active element comprises a polymer.

4. The vaso-occlusive device of claim 2, wherein the active element comprises a hydrogel.

5. The vaso-occlusive device of claim 4, wherein the hydrogel is one or both of a polyelectrolyte and thermoresponsive.

6. The vaso-occlusive device of claim 2, wherein the active element is a fiber comprising protein.

7. The vaso-occlusive device of claim 6, wherein the fiber comprising protein undergoes one or both of a thermally induced and pH induced phase transition or denaturation after being placed in the body.

8. The vaso-occlusive device of claim 2, wherein the active element is a polymer gel comprising a biocompatible polymer swollen with an aqueous ionic solution that will diffuse out of the gel, causing the gel to contract, upon contact with blood.

9. The vaso-occlusive device of claim 2, wherein the active element comprises a bioactive agent that elicits a biological reaction inside a body.

* * * * *

UNITED STATES PATENT AND TRADEMARK OFFICE
CERTIFICATE OF CORRECTION

PATENT NO. : 7,645,292 B2
APPLICATION NO. : 10/695151
DATED : January 12, 2010
INVENTOR(S) : Stephen C. Porter Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this

Sixteenth Day of November, 2010

David J. Kappos
*Director of the United States Patent and Trademark Office*